United States Patent
Ehrman

(10) Patent No.: US 9,867,763 B2
(45) Date of Patent: Jan. 16, 2018

(54) MODULAR EMULSION-BASED PRODUCT DIFFERENTIATION

(71) Applicant: Noxell Corporation, Hunt Valley, MD (US)

(72) Inventor: Matthew Clair Ehrman, Baltimore, MD (US)

(73) Assignee: Noxell Corporation, Hunt Valley, MD (US)

( * ) Notice: Subject to any disclaimer, the term of this patent is extended or adjusted under 35 U.S.C. 154(b) by 47 days.

(21) Appl. No.: 14/274,077

(22) Filed: May 9, 2014

(65) Prior Publication Data

US 2015/0321156 A1    Nov. 12, 2015

Related U.S. Application Data

(60) Provisional application No. 61/821,883, filed on May 10, 2013.

(51) Int. Cl.
| | | |
|---|---|---|
| *A61K 8/06* | (2006.01) | |
| *B01F 17/00* | (2006.01) | |
| *A61Q 19/00* | (2006.01) | |
| *B01F 17/54* | (2006.01) | |

(52) U.S. Cl.
CPC .............. *A61K 8/06* (2013.01); *A61K 8/068* (2013.01); *A61Q 19/00* (2013.01); *B01F 17/00* (2013.01); *B01F 17/0071* (2013.01); *A61K 2800/10* (2013.01); *A61K 2800/59* (2013.01)

(58) Field of Classification Search
CPC ...... B01F 2003/0071; B01F 2003/0826; B01F 2003/0838; B01F 17/00; B01F 17/0071; A61K 8/04; A61K 8/066; A61K 8/068; A61K 2800/10; A61K 2800/41; A61K 2800/59
See application file for complete search history.

(56) References Cited

U.S. PATENT DOCUMENTS

| | | | | |
|---|---|---|---|---|
| 2,299,693 | A | * | 10/1942 | Green ................... B41M 5/132 |
| | | | | 101/DIG. 29 |
| 4,254,105 | A | | 3/1981 | Fukuda |
| 5,163,010 | A | | 11/1992 | Klein et al. |
| 5,190,915 | A | | 3/1993 | Behan et al. |

(Continued)

FOREIGN PATENT DOCUMENTS

| | | |
|---|---|---|
| CN | 101896155 A | 11/2010 |
| CN | 102238931 A | 11/2011 |

(Continued)

OTHER PUBLICATIONS

Tadros, T. F., Future Developments in Cosmetic Formulations, International Journal of Cosmetic Science 14, 93-111 (1992).

(Continued)

*Primary Examiner* — Lakshmi Channavajjala
(74) *Attorney, Agent, or Firm* — Schwegman Lundberg & Woesnner, P.A.

(57) ABSTRACT

A micro-scale heterogeneous emulsion is provided. In some examples, the micro-scale heterogeneous emulsion can include at least two internal phases and an external phase. A method of producing a micro-scale heterogeneous emulsion is also disclosed herein. A method of providing a stable, custom cosmetic composition is also disclosed herein.

13 Claims, 8 Drawing Sheets
(3 of 8 Drawing Sheet(s) Filed in Color)

(56) References Cited

U.S. PATENT DOCUMENTS

| | | | |
|---|---|---|---|
| 5,304,310 | A | 4/1994 | Lang et al. |
| 5,304,334 | A * | 4/1994 | Lahanas ............... A61K 8/066 252/299.7 |
| 5,304,370 | A | 4/1994 | Hawkins et al. |
| 5,869,171 | A | 2/1999 | Shiveley et al. |
| 6,080,394 | A | 6/2000 | Lin et al. |
| 6,383,503 | B1 | 5/2002 | Bleckmann et al. |
| 6,783,766 | B2 | 8/2004 | Pate et al. |
| 7,109,268 | B2 | 9/2006 | Creutz et al. |
| 7,229,632 | B2 * | 6/2007 | Amalric ............... A61K 8/042 424/400 |
| 7,271,200 | B2 | 9/2007 | Scher et al. |
| 7,351,749 | B2 | 4/2008 | Divone et al. |
| 7,357,563 | B2 | 4/2008 | Phallen et al. |
| 7,544,718 | B2 | 6/2009 | Binder et al. |
| 7,683,119 | B2 | 3/2010 | Creutz et al. |
| 8,240,908 | B2 | 8/2012 | Williams et al. |
| 8,613,911 | B2 | 12/2013 | Corbo et al. |
| 8,616,760 | B2 | 12/2013 | Williams et al. |
| 2003/0064046 | A1 | 4/2003 | Omura et al. |
| 2004/0116539 | A1 | 6/2004 | Biercevicz et al. |
| 2006/0204469 | A1 | 9/2006 | Spengler et al. |
| 2006/0251605 | A1 | 11/2006 | Belmar et al. |
| 2007/0044824 | A1 | 3/2007 | Capeci et al. |
| 2007/0047384 | A1 | 3/2007 | McLaughlin et al. |
| 2007/0128137 | A1 | 6/2007 | Yoshimi et al. |
| 2007/0148116 | A1 * | 6/2007 | Seigneurin ............ A61K 8/39 424/70.12 |
| 2007/0264210 | A1 | 11/2007 | Robinson |
| 2007/0274932 | A1 | 11/2007 | Suginaka et al. |
| 2007/0280977 | A1 * | 12/2007 | Macian ............... A61K 8/066 424/401 |
| 2007/0297996 | A1 | 12/2007 | Tanner |
| 2008/0031085 | A1 | 2/2008 | McLaughlin et al. |
| 2008/0144427 | A1 | 6/2008 | Phallen |
| 2008/0299058 | A1 | 12/2008 | Saito et al. |
| 2009/0011035 | A1 | 1/2009 | Zukowski et al. |
| 2009/0012187 | A1 * | 1/2009 | Chu ............... A61K 9/113 516/54 |
| 2009/0073801 | A1 | 3/2009 | Danner et al. |
| 2009/0196836 | A1 | 8/2009 | Tanner et al. |
| 2009/0324525 | A1 | 12/2009 | Gianni |
| 2010/0028393 | A1 | 2/2010 | Jones |
| 2010/0080833 | A1 | 4/2010 | Rossow et al. |
| 2010/0272763 | A1 | 10/2010 | Nakamura |
| 2011/0223120 | A1 * | 9/2011 | Gaenzler ............ A61K 8/891 424/59 |
| 2011/0305102 | A1 | 12/2011 | Berger et al. |
| 2011/0305648 | A1 | 12/2011 | Knapek et al. |
| 2011/0305649 | A1 | 12/2011 | Lou et al. |
| 2011/0305652 | A1 | 12/2011 | Hilvert et al. |
| 2011/0305739 | A1 | 12/2011 | Royce et al. |
| 2011/0305778 | A1 | 12/2011 | Caggioni et al. |
| 2014/0335030 | A1 * | 11/2014 | Ehrman ............ A61K 8/345 424/59 |
| 2014/0336275 | A1 * | 11/2014 | Ehrman ............ A61Q 19/00 514/772 |

FOREIGN PATENT DOCUMENTS

| | | | |
|---|---|---|---|
| CN | 103108675 | A | 5/2013 |
| DE | 10247086 | A1 | 4/2004 |
| DE | 10 2006 049 054 | A1 | 4/2008 |
| EP | 2 140 852 | B1 | 10/2012 |
| FR | EP 1579845 | A2 * | 9/2005 ............ A61K 8/891 |
| JP | 02-174927 | A | 7/1990 |
| JP | 04-334311 | A | 11/1992 |
| JP | 10-503780 | A | 4/1998 |
| JP | 10-180088 | A | 7/1998 |
| JP | 10-509445 | A | 9/1998 |
| JP | 2002-338433 | A | 11/2002 |
| JP | 2004-285026 | A | 10/2004 |
| JP | 2005-089366 | A | 4/2005 |
| JP | 2007-501835 | A | 2/2007 |
| JP | 2008-31115 | A | 2/2008 |
| JP | 2009-161523 | A | 7/2009 |
| JP | 2010-513289 | A | 4/2010 |
| JP | 2010-132648 | A | 6/2010 |
| JP | 2010-138150 | A | 6/2010 |
| JP | 2011-246445 | A | 12/2011 |
| JP | 2013-216640 | A | 10/2013 |
| KR | 740598 | B1 * | 7/2007 |
| WO | WO-2006/010088 | A1 | 1/2006 |
| WO | WO-2012/119068 | A2 | 9/2012 |
| WO | WO-2014/182993 | A3 | 11/2014 |

OTHER PUBLICATIONS

Walstra, Pieter, Principles of Emulsion Formation, Chemical Engineering Science, vol. 48, No. 2, pp. 333-349, 1993.

O'Lenick, Jr., Anthony J., Silicone Emulsions and Surfactants, Journal of Surfactants and Detergents, vol. 3, No. 3 (Jul. 2000), pp. 387-393.

Whitesides, George M. et al., Synthesis of Composite Emulsions and Complex Foams with the use of Microfluidic Flow-Focusing Devices, small 2007, 3, No. 10, 1792-1802.

Steol CS-330 Product Bulletin, Stepan Company, Apr. 2009, 2 pages.

McIntyre Group, Ltd. Personal Care Product Guide, Apr. 2007, 28 pages.

Chudzikowski, R. J., Guar gum and its applications, Journal of the Society of Cosmetic Chemists 22 (1971) pp. 43-60.

Methocel Cellulose Ethers Technical Handbook, The Dow Chemical Company, Sep. 2002, 32 pages.

Kulicke et al., Rheological characterization of the dilatant flow behavior of highly substituted hydroxypropylmethyl-cellulose solutions in the presence of sodium lauryl sulfate, Colloid & Polymer Science, vol. 276, No. 7 (1998), pp. 617-626.

Methocel Cellulose Ethers, Amerchol Corporation—subsidiary of the Dow Chemical Company, Aug. 2005, 32 pages.

"Canadian Application Serial No. 2,912,226, Office Action mailed Oct. 6, 2016", 5 pgs.

"Canadian Application Serial No. 2,912,226, Voluntary Amendment filed Nov. 10, 2015", 4 pgs.

"International Application Serial No. PCT/US2014/037434, International Preliminary Report on Patentability mailed Nov. 19, 2015", 10 pgs.

"International Application Serial No. PCT/US2014/037434, International Search Report mailed Nov. 5, 2014", 5 pgs.

"International Application Serial No. PCT/US2014/037434, Written Opinion mailed Nov. 5, 2014", 8 pgs.

"Japanese Application Serial No. 2016-513107, Office Action mailed Nov. 8, 2016", (w/ English Translation), 7 pgs.

Clausse, D, "33. Mass Transfers Within Emulsions Studied by Differential Scanning Calorimetry (DSC)—Application to Composition Ripening and Solid Ripening", in: Mass Transfer—Advanced Aspects, Edited by Dr. Hironori Nakajima, [Online] Retrieved from the Internet : <http://cdn.intechopen.com/pdfs-wm/2354>, (2011), 743-778.

Kaneko, Akihisa, "Oil-in-water multiphase emulsions for cosmetics and pharmaceuticals and their manufacture", *Abstract* 113: 217776u, *Chemical Abstracts*, vol. 113, No. 23, (Jul. 6, 1990), p. 356.

"Chinese Application Serial No. 201480024859.4, Office Action mailed Feb. 3, 2017", (w/ English Translation), 33 pgs.

"European Application Serial No. 14731105.4, Communication Pursuant to Article 94(3) EPC mailed Feb. 23, 2017", 3 pgs.

"Japanese Application Serial No. 2016-513107, Response filed Feb. 7, 2017 to Office Action mailed Nov. 8, 2016", (w/ English Translation of Claims), 7 pgs.

Clausse, D., et al., "Chapter 33—Mass Transfers Within Emulsions Studied by Differential Scanning Calorimetry (DSC)—Application to Composition Ripening and Solid Ripening", *in: Mass Transfer—Advanced Aspects*, (2011), 743-778.

U.S. Appl. No. 14/274,089, filed May 9, 2014, Matthew Clair Ehrman et al.

(56) References Cited

OTHER PUBLICATIONS

U.S. Appl. No. 14/274,104, filed May 9, 2014, Matthew Clair Ehrman et al.
"Canadian Application Serial No. 2,912,226, Response filed Apr. 3, 2017 to Office Action dated Oct. 6, 2016", 19 pgs.
"Canadian Application Serial No. 2,912,226, Office Action dated Jun. 16, 2017", 4 pgs.
"Chinese Application Serial No. 201480024859.4, Response filed Jun. 19, 2017 to Office Action dated Feb. 3, 2017", (w/ English Translation of Claims), 10 pgs.
"Japanese Application U.S. Appl. No. 2016-513107, Office Action dated Aug. 1, 2017", (w/ English Translation), 6 pgs.

\* cited by examiner

MODULAR EMULSION-BASED PRODUCT DIFFERENTIATION

TECHNICAL FIELD

The present disclosure generally relates to micro-scale heterogeneous emulsions and methods relating thereto.

BACKGROUND

Expanding product variety and increasing the efficiency of operations are often challenging issues for manufactures. In this regard, the expansion of product variety and/or increase in the efficiency of operations may have to account for variables such as consumer preference, economic considerations, product performance requirements, as well as technical hurdles that may be associated with producing a product, such as those that may occur when attempting to produce complex, multiphase substances.

One method used to manufacturer consumer products that contain complex, multiphase substance, such as emulsions, is the batch process. Emulsions produced using the batch process frequently contain a water-immiscible phase and an aqueous phase. Often, a first step in the production of such emulsions involves separately preparing the aqueous phase and the water-immiscible phase. The final product may be an emulsion produced by shearing the aqueous and water-immiscible phases in large vessels. Although batch processing may offer some advantages like a variability in the production rate, batch processing may present disadvantages like long processing times and difficulties in scaling up to larger batches. In this regard, a manufacturer may experience surpluses and/or stock-outs of certain consumer products directly or indirectly because of the relatively long processing times for batch processing and difficulties in scaling up. Furthermore, these disadvantages may also impact the variety of products a manufacturer may offer.

One approach for expanding product variety and increasing the efficiency of producing end products is to prolong the point of product differentiation (i.e. defer when the end-product acquires its unique identities). However, such strategies for reducing the lead-time for redesigning products often present unique challenges that must be solved and may vary on the type of end-product desired. For example, with respect to the production of complex, multiphase substances, the unpredictability of such substances may present technical hurdles like instability when attempting to prolong the point of product differentiation. Thus, there is exists a need for developing new processes for producing consumer products that contain complex, multiphase substances than can expand product variety and increase the efficiency of producing end products without some or all of the drawbacks associated with other manufacturing methods like batch processing.

SUMMARY

In some examples, a consumer product comprising a micro-scale heterogeneous emulsion is disclosed herein, the micro-scale heterogeneous emulsion comprising: a first internal phase; a second internal phase; an external phase; wherein the first internal phase and the second internal phase are each stabilized within the external phase; and wherein the second internal phase differs from the first internal phase in chemical makeup.

BRIEF DESCRIPTION OF THE DRAWINGS

The patent or application file contains at least one photograph executed in color. Copies of this patent or patent application with color photograph(s) will be provided by the Office upon request and payment of the necessary fee.

While the specification concludes with claims, it is believed that the same will be better understood from the following description taken in conjunction with the accompanying drawings in which:

DETAILED DESCRIPTION

Figure 1:
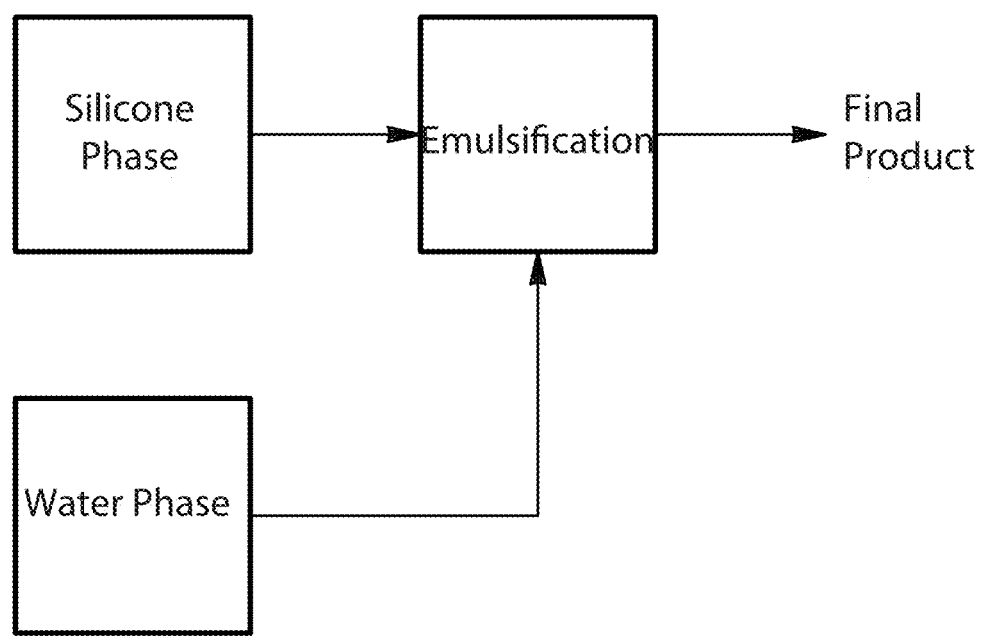
FIG. 1 is a schematic representation of a batch process.

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Combining" refers to a mixing process where the common external phases are liquid-liquid blended thereby dispersing the individual dispersed phases into a composite emulsion.

"Composition" means a mixture of different constituent chemicals.

"Constant internal phase" means that the chemical makeup of the droplets which make up the internal phase of an emulsion is such that the chemical makeup is uniform with the droplets. Said differently, the droplets suspended within the external phase typically contain the same ingredients at similar concentrations "Consumer product" includes, but is not limited, to diapers; bibs; wipes; products for and/or methods relating to treating hair (human, dog, and/or cat), including, bleaching, coloring, dyeing, conditioning, shampooing, styling; deodorants and antiperspirants; personal cleansing; cosmetics; skin care products including application of creams, lotions, and other topically applied products for consumer use; shaving products; products for and/or methods relating to treating fabrics, hard surfaces and any other surfaces in the area of fabric and home care, including air care, car care, dishwashing, fabric conditioning (including softening), laundry detergent, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

"Cosmetic composition" means a composition suitable for topical application on mammalian keratinous tissue. Non-limiting examples of cosmetic compositions include foundations, powders, concealers, blushes, make-up removers, hair removers, facial hair removers, bronzers, mascaras, eye shadows, eye liners, lip glosses, lip colors, lip liners, nail polishes, skin creams, facial creams, facial cleansers, sunscreen lotions, body lotions, shaving gels, shaving foams, shaving creams, conditioners, and aftershaves.

"Derivatives" include, but are not limited to, amide, ether, ester, amino, carboxyl, acetyl, and/or alcohol derivatives of a given chemical.

"Dispersion" refers to a suspension of solid particles within a continuous phase.

"Droplet coalescence" refers to a process where at least two discrete emulsion droplets aggregate and eventually rupture to form a single emulsion droplet.

"Emulsion" refers to a colloidal suspension of at least two immiscible (non-soluble) liquid phases.

"External phase" refers to the continuous component of an emulsion in which at least one other dispersed component is suspended within.

"Extract" means material that may be obtained by the following procedure: Place the indicated portion of dried plant material (stem, bark, leaves, etc.) in a conical glass percolator. Add the indicated percentage of extraction solvent in a w/w ratio of 1 part plant material to 2 parts extraction solvent. When the indicated percentage of extraction solvent is less than 100%, the remaining solvent is water (e.g., 95% ethanol with 5% water, 50% ethanol with 50% water, etc.). Allow the extraction to proceed for about 16 to about 24 hours. Collect the percolate, and repeat the above process until the resulting percolate is substantially free from plant additional extract. Combine the percolates, evaporate to dryness under reduced pressure, and store the resulting extract under nitrogen at less than 4 degrees Celsius.

"Fabric care composition" includes, unless otherwise indicated, fabric softening compositions, fabric enhancing compositions, fabric freshening compositions, and combinations thereof.

"Free of" means that the stated ingredient has not been added to the composition. However, the stated ingredient may incidentally form as a byproduct or a reaction product of the other components of the personal care composition.

"Functionally modified polymer" refers to a polymer that has select functional groups polymerized into a molecule in order to alter its chemical properties.

"Glycerol" means a tri-hydroxyl alcohol.

"Heterogeneous" means consisting of non-uniform ingredients or dissimilar constituents.

"High internal phase emulsion" refers to an emulsion in which the internal phase volume fraction exceeds the 0.74 close packing limit for monodisperse phases.

"High shear mixing" refers to a regime of turbulent mixing where the regime has a Reynolds number of about 10,000 or greater.

"Homogeneous" means consisting of uniform ingredients or similar constituents.

"Hyperpigmentation" refers to an area of skin wherein the pigmentation is greater than that of an adjacent area of skin (e.g., a pigment spot, an age spot, and the like).

"Improve skin condition" or "improving skin condition" means effecting a visually and/or tactilely perceptible positive change, or benefit, in skin appearance and feel. Benefits that may be provided include, but are not limited to, one or more of the following: Reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); skin lightening; preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, etc.

"Internal phase" refers to the dispersed component of an emulsion.

"Keratinous tissue" refers to keratin-containing layers disposed as the outermost protective covering of mammals which includes, but is not limited to, skin, hair, nails, cuticles, etc.

"Low shear mixing" refers to a regime of laminar mixing where the regime has a Reynolds number of about 2000 or less.

"Micro-scale" means having at least one linear dimension approximately between 0.001 microns and 100 microns.

"Pickering emulsion" refers to an emulsion where two immiscible liquids are stabilized by solid particles that absorb at the interface of the two phases.

"Polar solvent" refers to a molecule which has an electric dipole or multipole moment, the strength of the electric dipole or multipole moment dependent on the difference in electronegativity between atoms and structure of the molecule.

"Salts" include, but are not limited to, sodium, potassium, calcium, ammonium, manganese, copper, and/or magnesium salts of a compound.

"Signs of skin aging" include but are not limited to, all outward visibly and tactilely perceptible manifestations, as well as any macro- or micro-effects due to the aging of keratinous tissue. These signs may result from processes that include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

"Silicone" refers to a silicone oil.

"Skin care active" means a substance that, when applied to the skin, provides a benefit or improves the skin's condition. It is to be understood that skin care actives are useful not only for application to skin, but also to hair, nails and other mammalian keratinous tissue.

"Stabilize" means to make or prepare a colloidal structure that does not separate into its individual component separate phases when the colloidal structure is subject to 40° C. and 1 atm for 30 days.

"Stable" means a colloidal structure that does not separate into its individual component separate phases when the colloidal structure is subject to 40° C. and 1 atm for 30 days.

"Substantially free"" means an amount of a material that is less than 1%, 0.5%, 0.25%, 0.1%, 0.05%, 0.01%, or 0.001% by weight of a composition.

"Surfactant" refers to surface active ingredients than can lower the interfacial tension between two chemical interfaces. Surfactants may act as emulsifying agents for two immiscible liquid phases by lowering the interfacial tension between the two phases. A surfactant may have amphiphilic properties due to its chemical structure.

It has been surprisingly discovered that micro-scale heterogeneous emulsions may deliver consistent end user experiences and similar efficacy with respect to the delivery of actives as compared to emulsions produced by conventional processes. Additionally, the process for producing micro-scale heterogeneous emulsions may be used to prolong the point of product differentiation, which in turn may expand product varieties and increase the efficiency of production. Micro-scale heterogeneous emulsions may also be used to provide consumers with customizable, stable cosmetic compositions.

It has been found that the use of micro-scale heterogeneous emulsions may provide several advantages over conventional batch processes in the production of consumer products. For example, it has been found that the use of micro-scale heterogeneous emulsions can result in a ~500% to ~600% increase in total batch output, an ~80% reduction in batch cycle time for making consumer products, an ~80% reduction in the amount of cleaning & sanitization required during the production of consumer products, and about a 68% reduction in the number of weighings (of ingredients) required, as compared to a conventional batch process.

Figure 2:
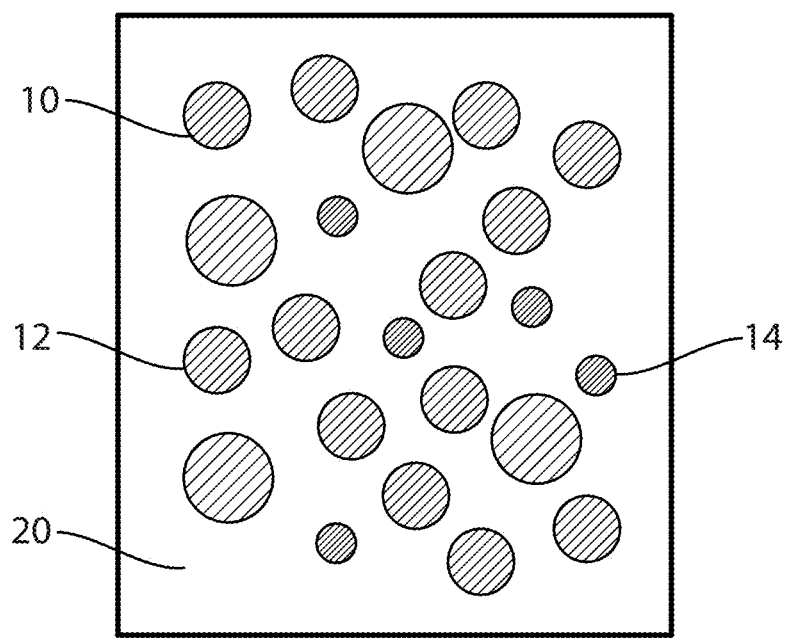
FIG. 2 is a graphic depiction of an emulsion made by the batch process.

The micro-scale heterogeneous emulsions described herein may differ from conventional emulsions, such as those made by a batch process or other emulsification technique such as continuous process, in several respects. As illustrated in FIG. 1, some conventional emulsions are made by emulsifying a water phase with a silicone phase to form a final product. As shown in FIG. 2, the process of FIG. 1 typically results in a homogeneous emulsion 20 where there is a constant internal phase made up of droplets that may vary in size. Referring to FIG. 2, the droplets 10 12 and 14, while they may vary in size, do not usually vary in chemical makeup.

Figure 3:
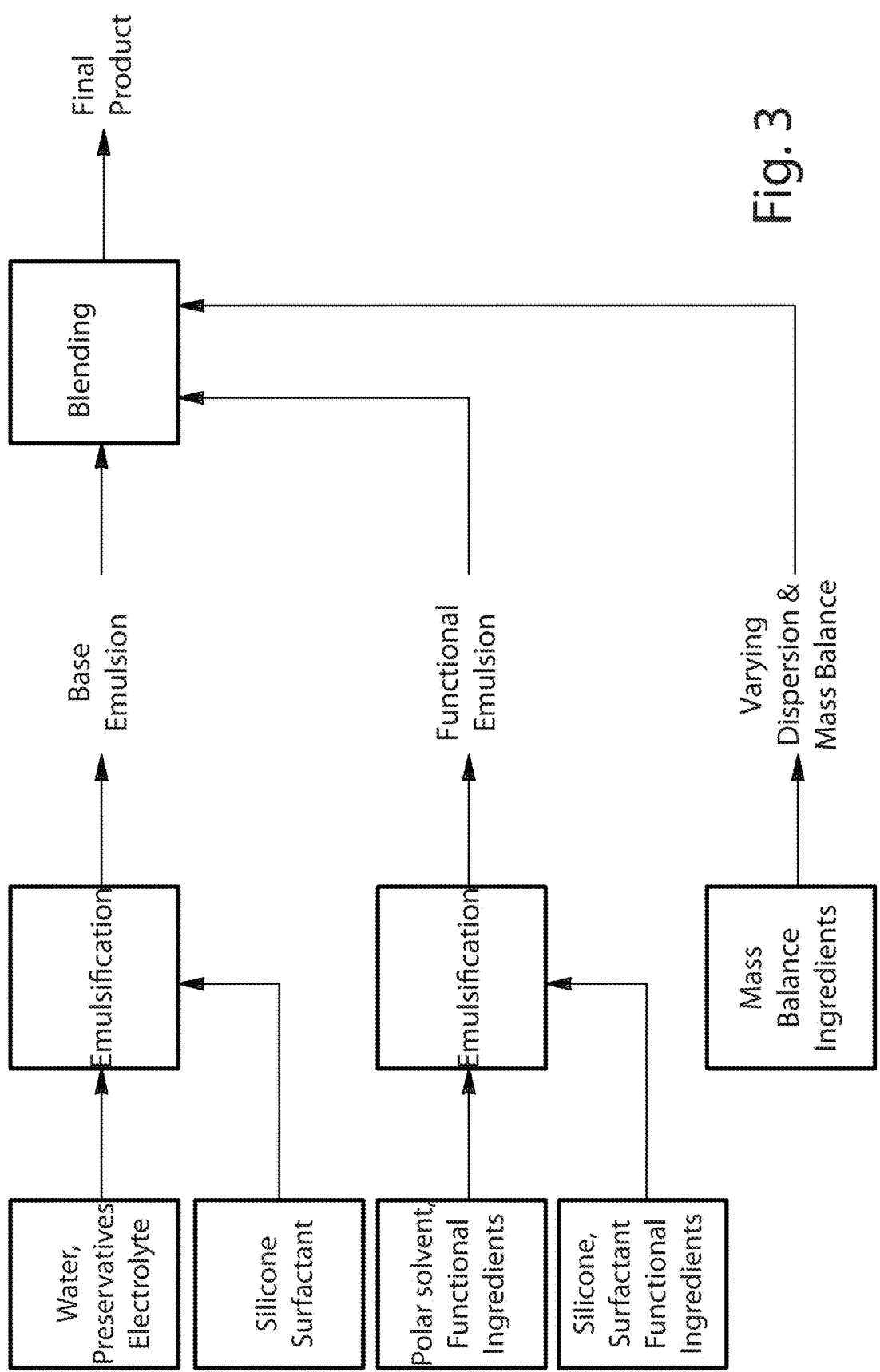
FIG. 3 is a schematic representation of an embodiment of a process to produce a micro-scale heterogeneous emulsion.

In contrast, micro-scale heterogeneous emulsions may be made by a variety of process, one of which is illustrated in FIG. 3. Referring to FIG. 3, a final product that includes a micro-scale heterogeneous emulsion may be made by combining a base emulsion that may be prepared by emulsifying a water phase containing preservatives and electrolytes with a silicone phase containing silicones and a surfactant, at least one dispersion that may contain mass balance ingredients, with at least one functional emulsion that may be prepared by emulsifying a polar phase including a polar solvent and one or more functional ingredients with a silicone phase containing silicone, a surfactant, and one or more functional ingredients.

Figure 4:
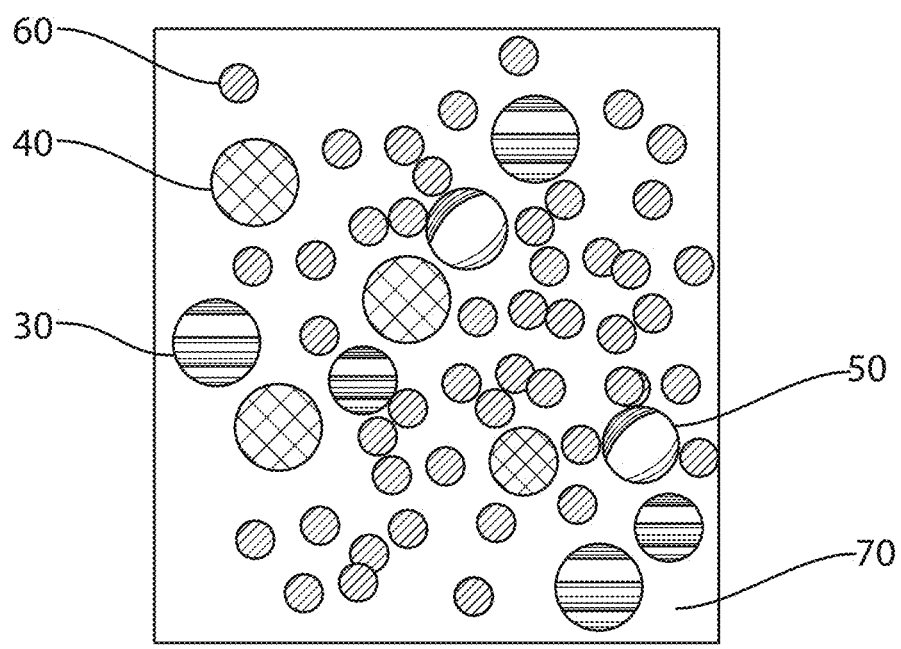
FIG. 4 is a graphic depiction of a micro-scale heterogeneous emulsion.
Figure 5:
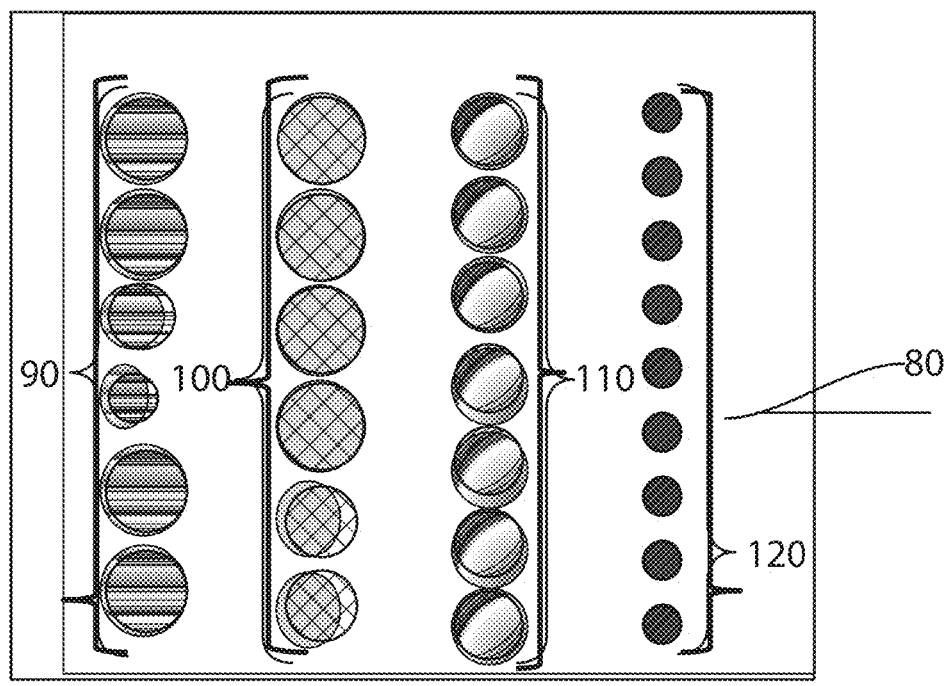
FIG. 5 is a graphic depiction of a micro-scale heterogeneous emulsion.

As shown in FIG. 4, the process of FIG. 3 may result in a micro-scale heterogeneous emulsion 70. Referring to FIG. 4, droplet 30, droplet 40, droplet 50, and droplet 60 each represent droplets with a different chemical makeup from the other. These distinct droplets in turn may form a microstructure where there is more than one unique internal phase within the continuous phase. The micro-scale heterogeneous emulsion 80 thus may contain several internal phases as shown in FIG. 5. Referring to FIG. 5, the plurality of droplets 90 represents one unique internal phase, the plurality of droplets 100 represents a second unique internal phase, the plurality of droplets 110 represents a third unique internal phase, and the plurality of droplets 120 represents a fourth unique internal phase, that together with the external phase make up the micro-scale heterogeneous emulsion 80. Thus in contrast to conventional emulsions, the internal phase droplet composition of a micro-scale heterogeneous emulsion may be varied intentionally and systemically depending on the final product desired.

Figure 6:
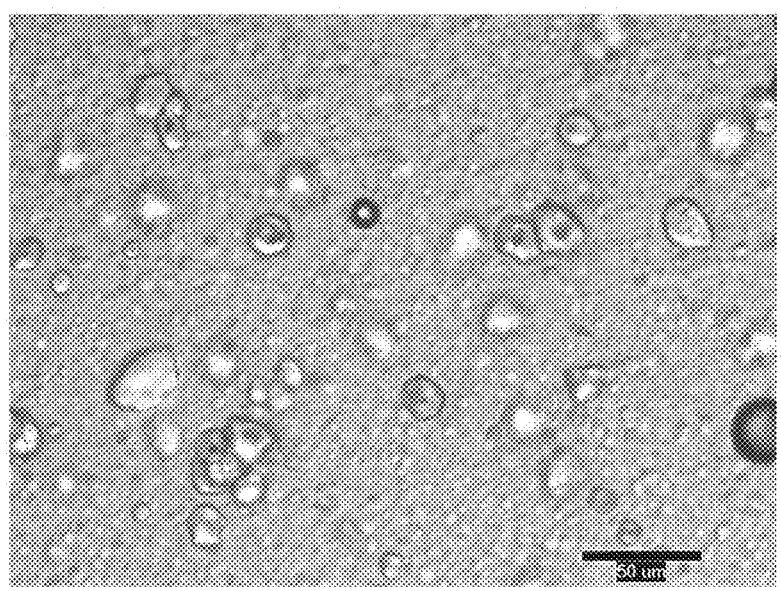
FIG. 6 is a portion of a micro-scale heterogeneous emulsion.
Figure 7:
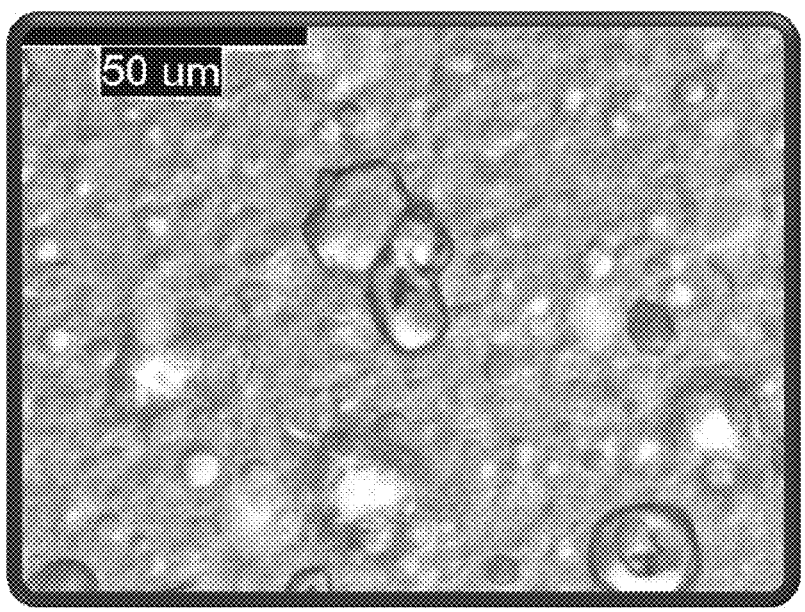
FIG. 7 is an enlargement of a portion of the micro-scale heterogeneous emulsion shown in FIG. 6.

To illustrate that micro-scale heterogeneous emulsions may comprise more than one internal phase, a micro-scale heterogeneous emulsion was prepared by combining a base emulsion with two different functional emulsions. One functional emulsion included a fluorescein dye in the polar phase and the second functional emulsion included a nile-red dye in the polar phase. As can be observed from FIG. 6 and FIG. 7, after combination of the base emulsion and the functional emulsions, the two different dyes do not appear to co-localize to the same droplets. In fact, the red droplets and green droplets appear distinct throughout the continuous phase. These data suggest that micro-scale heterogeneous emulsions may comprise at least two internal phases.

Micro-scale heterogeneous emulsions were also evaluated for their ability to deliver a skin care active. For comparison, a conventional emulsions made by a batch process was included in the study. In Example 2, a series of in vitro skin penetration studies were conducted over a 6 hr time period to assess the penetration of radiolabeled niacinamide from micro-scale heterogeneous emulsions and from an emulsion made by the batch process (i.e. batch emulsion). The emulsions were topically applied to split-thickness human cadaver skin. A Franz diffusion cell system was used to measure the amount of penetration of the radiolabeled niacinamide thru the cadaver skin.

Figure 8:
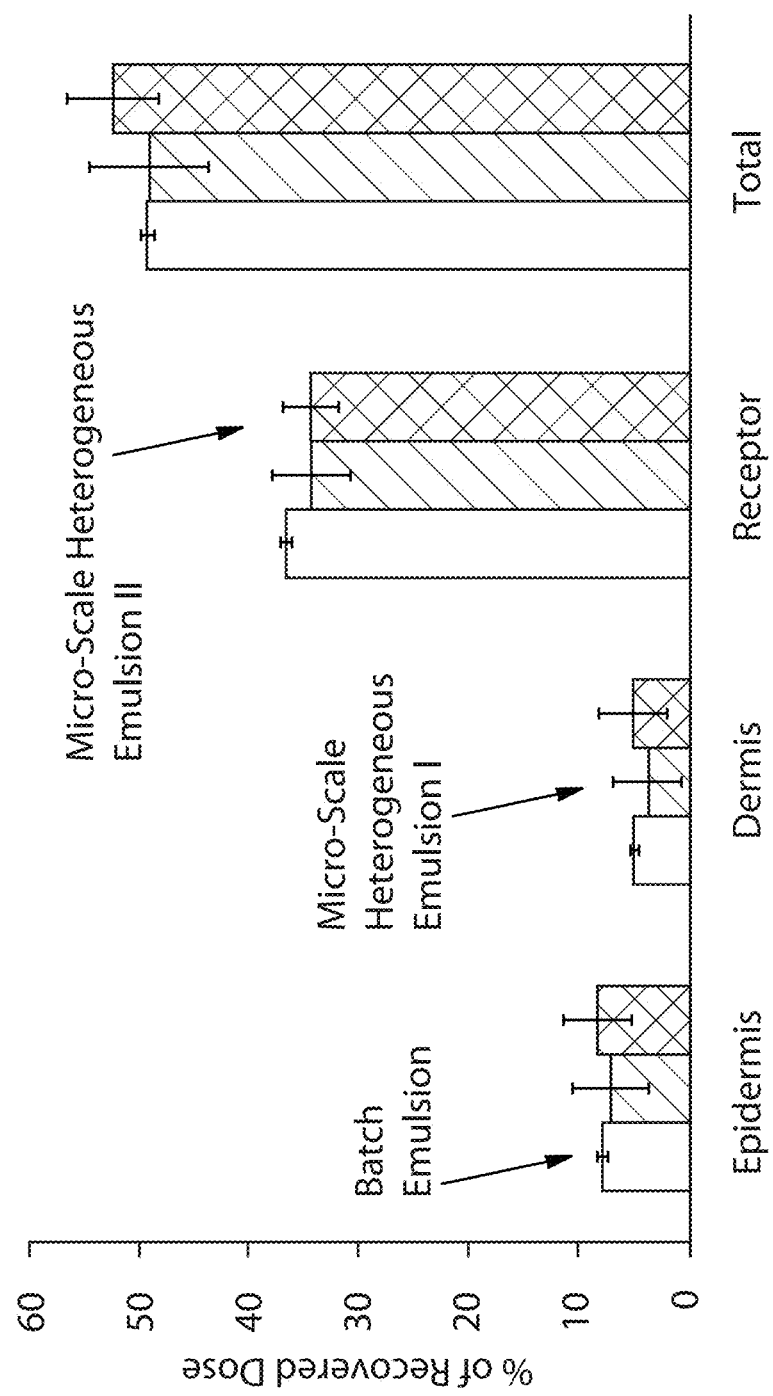
FIG. 8 is a graph illustrating the niacinamide penetration of three different emulsions.

Referring to FIG. 8, the individual and total percentage dose of niacinamide recovered from the epidermis, dermis, and the Franz Cell Receptor after application of the emulsions from Example 2 are plotted. No significant difference was observed between the either of the micro-scale heterogeneous emulsions and the batch emulsion evaluated with respect to niacinamide penetration into either the epidermal or dermal layers of the skin. Moreover, no significant difference was observed between the micro-scale heterogeneous emulsions and the batch emulsion with respect to niacinamide penetration into the Franz Cell Receptor or in the total amount of niacinamide recovered. The data suggests that micro-scale heterogeneous emulsions may deliver skin care actives with similar efficacy as compared to certain conventional emulsions.

Micro-scale heterogeneous emulsions were also evaluated for their consumer acceptance. A number of panelists were provided a foundation made from an emulsion that was made by a conventional batch process (denoted as "Conventional Foundation") and a foundation made from a micro-scale heterogeneous emulsion (denoted as "Inventive Foundation"). Individuals were instructed to use each foundation normally for a period of 5 days. Half of the panelists were instructed to use the Conventional Foundation for 5 days and then to switch to the Inventive Foundation for 5 days. The other half of the panelists were instructed to use the Inventive Foundation for 5 days and then to switch to the Conventional Foundation for the next 5 days. Panelists were not informed which of the foundations were new (i.e. made from a micro-scale heterogeneous emulsion) or conventional. Panelists were asked to complete a questionnaire at day 5 and day 10 during the test period. The questionnaire instructed the panelists to rate the two different foundations on metrics such as how much consistency was provided, ease of application, shade acceptance, and ability to moisturize the skin. On these metrics, there was no significant difference in the response of panelists suggesting that some consumers may view cosmetic compositions comprising micro-scale heterogeneous emulsions as acceptable or equivalent to cosmetic compositions comprising conventional emulsions.

A micro-scale heterogeneous emulsion may be prepared by combining two or more preliminary emulsions using either low shear mixing or high shear mixing by any method known in the art. Preliminary emulsions may be prepared by high or low shearing by any method known in the art. Base emulsions, structural emulsions, and functional emulsions may be non-limiting examples of preliminary emulsions. Whether a preliminary emulsion used is a base emulsion, structural emulsion, functional emulsion, or some other form of an emulsion is based on the desired function or rationale for including that emulsion within the micro-scale heterogeneous emulsion. In some examples, a base emulsion may represent an emulsion that is free of an active and a structurant or substantially free of an active and a structurant. In some examples, a structural emulsion may include one or more structurants. In some examples, a functional emulsion may include one or more functional ingredients. A functional ingredient is an ingredient included to provide a function non-structural in nature, such that provided by an active. In some examples, it may be desirable to prepare at least one preliminary emulsion that is free of water or substantially free of water in order to limit microbial growth and allow for long term storage. One or more dispersions may also be combined with the one or more preliminary emulsions when preparing the micro-scale heterogeneous emulsion. In some examples, it may be desirable to combine at least two preliminary emulsions by low shear mixing. In some examples, it may be desirable to combine at least one dispersion with the preliminary emulsions by low shear mixing. In some examples, a solution may combined with the one or more preliminary emulsions. In some examples, the micro-scale heterogeneous emulsion may comprise at least one high internal phase emulsion. Non-limiting examples of preliminary emulsions include water-in-oil emulsions, oil-in-water emulsions, and water-in-silicone emulsions. For example, oil-in-water emulsions contain oil droplets that are suspended within a continuous, aqueous medium.

When designing a micro-scale heterogeneous emulsion, the external phase solvents should be miscible/soluble at the final relative ratios with each other such that there are no significant thermodynamic energy drivers preventing the dissolution into the final external phase. Without being limited by theory, it has been observed that droplet coalescence may promote instability within micro-scale heterogeneous emulsions. Thus, droplet coalescence should be minimized. This can be accomplished by reducing or eliminating the quantity of destabilizing constituents within a preliminary emulsion. Destabilizing constituents are generally classes of ingredients that may partition at the interface of a multi-phase system. Non-limiting examples of destabilizing constituents include benzyl alcohol, ethyl alcohol, and phenoxyalcohol. Thus, in some examples, the preliminary emulsions may be free of benzyl alcohol, ethyl alcohol, phenoxyalcohol, and combinations thereof.

In some examples, the micro-scale heterogeneous emulsion may include two or more internal phases and an external phase. In some examples, the micro-scale heterogeneous emulsion may include three internal phases and an external phase. In some examples, the micro-scale heterogeneous emulsion may include four internal phases and an external phase. In other examples, the micro-scale heterogeneous emulsion may include more than four internal phases and an external phase. In some examples, the one or more internal phases are each stabilized within the external phase of the micro-scale heterogeneous emulsion. In some examples, at least one of the internal phases is structural such that the internal phase comprises at least one structurant. In some examples, at least one of the internal phases is functional such that the internal phase comprises at least one functional ingredient.

The average droplet size of an internal phase within the micro-scale heterogeneous emulsion may range, for example, from 0.5 microns to 3 microns, from to 0.5 microns to 5 microns, from 0.5 microns to 10 microns, or from 0.5 microns to 100 microns. In certain examples, the average droplet size may be smaller than 0.5 microns. The average droplet size of the micro-scale heterogeneous emulsion may vary depending on the method used to combine the one or more preliminary emulsions with the optional one or more dispersions.

In some examples, the micro-scale heterogeneous emulsion may include one or more stabilizers to stabilize the one or more internal phases within the external phase. The stabilizing amount of stabilizer required to stabilize the internal phases within the external phase may vary. The stabilizer may be present in the internal phases and/or the external phase of the micro-scale heterogeneous emulsion. Non-limiting examples of stabilizers include surfactants and functionally modified polymers. Non-limiting examples of surfactants that may be used as stabilizers include silicone surfactants, non-ionic surfactants, ionic surfactants such as cationic surfactants and anionic surfactants, and combinations thereof.

Suitable stabilizers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof.

Linear or branched type silicone emulsifiers may also be used as stabilizers. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu.

Stabilizers may also include emulsifying silicone elastomers. Suitable emulsifying silicone elastomers may include at least one polyalkyl ether or polyglycerolated unit. Polyoxyalylenated emulsifying silicone elastomers that may be used include those sold by Shin-Etsu Silicones under the names KSG-21, KSG-20, KSG-30, KSG-31, KSG-32, KSG-33; KSG-210 (dimethicone/PEG-10/15 crosspolymer dispersed in dimethicone); KSG-310 (PEG-15 lauryl dimethicone crosspolymer); KSG-320 (PEG-15 lauryl dimethicone crosspolymer dispersed in isododecane); KSG-330 (PEG-15 lauryl dimethicone crosspolymer dispersed in triethylhexanoin), KSG-340 (PEG-10 lauryl dimethicone crosspolymer and PEG-15 lauryl dimethicone crosspolymer). Other silicone emulsifying elastomers are supplied by Dow Corning™, including PEG-12 dimethicone crosspolymers (DC 9010 and 9011). Other suitable silicone emulsifiers sold by Dow Corning include DC9010 and DC9011. Polyglycerolated emulsifying silicone elastomers are disclosed in PCT/WO 2004/024798. Such elastomers include Shin-Etsu's KSG series, such as KSG-710 (dimethicone/polyglycerin-3 crosspolymer dispersed in dimethicone); or lauryl dimethicone/polyglycerin-3 crosspolymer dispersed in a variety of solvent such as isododecane, dimethicone, triethylhexanoin, available as KSG-810, KSG-820, KSG-830, or KSG-840 from Shin-Etsu.

More non-limiting examples of stabilizers are disclosed in U.S. Pat. No. 3,755,560, 4,421,769, and McCutcheon's, *Emulsifiers and Detergents*, 2010 Annual Ed., published by M. C. Publishing Co. Other suitable stabilizers are further described in the Personal Care Product Council's *International Cosmetic Ingredient Dictionary and Handbook*, Thirteenth Edition, 2006, under the functional category of "Surfactants—Emulsifying Agents."

In certain examples, the micro-scale heterogeneous emulsion may also be a Pickering emulsion. The micro-scale heterogeneous emulsion may be a Pickering emulsion and include at least one functionally modified polymer in the external phase and/or internal phases. Non-limiting examples of functionally modified polymers include alkyl-modified silicone polymers; silicone polyethers; silicone quaternary compounds like silicone dialkyl quats, silicone fatty amido quats, and silicone polyether fatty quats; and silicone amines. Some non-limiting examples of functionally modified polymers are available from Siltech Corporation (Ontario, Canada) and sold under the tradenames: Silsurf A004, Silfsurf A008, Siltech OP-12, Silquat 3180, Silquat D2, Silamine A0 EDA, Silamine T-SA, and Silamine DG-50.

The external phase and internal phases of the micro-scale heterogeneous emulsion may include one or more solvents. Non-limiting examples of solvents include aqueous polar solvents (e.g. water) and non-aqueous polar solvents. Non-limiting examples of polar solvents include glycol-based polar solvents and glycerine-based polar solvents. Non-limiting examples of classes of non-aqueous polar solvents include monohydroxy alcohols, diols, triols, glycerol esters, and polyglycols. Non-limiting specific examples of non-aqueous polar solvents include ethanol, methanol, propanol, isopropanol, butanol, ethylene glycol, propylene glycol, dipropylene glycol, glycerol, glyceryl tripropionate, glyceryl tributyrate, polyethylene glycol, and mixtures thereof.

The external phase and internal phases of the micro-scale heterogeneous emulsion may include one or more preservatives. Non-limiting examples of preservatives include alkyl esters of para-hydroxybenzoic acid. Other useful preservatives include hydantoin derivatives such as 1,3-bis(hydroxymethyl)-5,5-dimthylhydantoin, propionate salts, and a variety of quaternary ammonium compounds such as benzalkonium chloride, quaternium 15 (Dowicil 200), benzethonium chloride, and methylbenzethonium chloride. Other examples of suitable preservatives include disodium EDTA, phenoxyethanol, methyl paraben, propyl paraben, imidazolidinyl urea (commercially available as Germall 1157), sodium dehydroacetate and benzyl alcohol. The preservatives should be selected having regard for the use of the composition and possible incompatibilities between the preservatives and other ingredients in the emulsion.

The external phase and internal phases of the micro-scale heterogeneous emulsion may include one or more colorants. In some examples, one or more colorants may be included in one or more dispersions and combined with the one or more preliminary emulsions to form the micro-scale heterogeneous emulsion. In some examples, one or more colorants may be included in one or more preliminary emulsions to form the micro-scale heterogeneous emulsion. A colorant may be in the form of a pigment. As used herein, the term "pigment" means a solid that reflects light of certain wavelengths while absorbing light of other wavelengths, without providing appreciable luminescence. Useful pigments include, but are not limited, to those which are extended onto inert mineral(s) (e.g., talk, calcium carbonate, clay) or treated with silicone or other coatings (e.g., to prevent pigment particles from re-agglomerating or to change the polarity (hydrophobicity) of the pigment. Pigments may be used to impart opacity and color. Any pigment that is generally recognized as safe (such as those listed in C.T.F.A. cosmetic Ingredient Handbook, $3^{rd}$ Ed., cosmetic and Fragrance Association, Inc., Washington, D.C. (1982), herein incorporated by reference) can be employed in the micro-scale heterogeneous emulsions described herein. Useful pigments include body pigment, inorganic white pigment, inorganic colored pigment, pearling agent, and the like. Specific examples are talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, polyethylene powder, methacrylate powder, polystyrene powder, silk powder, crystalline cellulose, starch, titanated mica, iron oxide titanated mica, bismuth oxychloride, and the like. The aforementioned pigments can be used independently or in combination.

Additional examples of pigments include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Other useful pigments are disclosed in U.S. Pat. No. 5,688,831, to El-Nokaly et al., issued Nov. 18, 1997. Also useful herein are pigments such as nanocolorants from BASF and multi-layer interference pigments such as Sicopearls from BASF. The pigments may be surface treated to provide added stability of color and ease of formulation. In addition, it may be useful to treat the pigments with a material that is compatible with silicones. Particularly useful treatments include polysiloxane treatments such as those disclosed in U.S. Pat. No. 5,143,722. Pigments may have a primary average particle size of from about 5 nm to about 100,000 nm, from about 50 nm to about 5,000 nm, or from about 100 nm to about 1000 nm.

Other useful colorants include aluminum, barium or calcium salts or lakes. Some other examples of colorants include Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake. A colorant may also be a dye. Suitable examples include Red 6, Red 21, Brown, Russet and Sienna dyes and mixtures thereof.

The external phase and internal phases of the micro-scale heterogeneous emulsion may include one or more structuring agents that can be used to increase viscosity, thicken, solidify, or provide solid or crystalline structure to micro-scale heterogeneous emulsion. In some examples, a preliminary emulsion may include one or more structuring agents. Structuring agents are typically grouped based on solubility, dispersibility, or phase compatibility. Examples of aqueous structuring agents include polymeric agents, natural or synthetic gums, polysaccharides, and the like. Polysaccharides and gums may be suitable aqueous phase thickening agents. Suitable classes of polymeric structuring agents include but are not limited to carboxylic acid polymers, polyacrylamide polymers, sulfonated polymers, high molecular weight polyalkylglycols or polyglycerins, copolymers thereof, hydrophobically modified derivatives thereof, and mixtures thereof.

Examples of oil structuring agents include silicone and organic based materials. Suitable oil structuring agents may be silicone based, such as silicone elastomers, silicone gums, silicone waxes, and linear silicones having a degree of polymerization allowing the silicone to increase the viscosity. Examples of silicone structuring agents include, but are not limited to, silicone elastomers, silicone gums, and silicone waxes. Suitable silicone elastomers may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silsesquioxane crosspolymers like KSP-100, KSP-101, KSP-102, KSP-103, KSP-104, KSP-105, available from Shin-Etsu, hybrid silicone powders that contain a fluoroalkyl group like KSP-200, available from Shin-Etsu, which is a fluoro-silicone elastomer, and hybrid silicone powders that contain a phenyl group such as KSP-300, available from Shin-Etsu, which is a phenyl substituted silicone elastomer; and DC 9506 available from Dow Corning.

Examples of silicone elastomer dispersions include dimethicone/vinyl dimethicone crosspolymers supplied by a variety of suppliers including Dow Corning Corporation under the tradenames DC9040 or DC9041, Momentive under the tradename SFE 839, or Shin-Etsu Silicones under the tradenames KSG-15, 16, 18. KSG-15 has the INCI name cyclopentasiloxane (and) dimethicone/vinyl dimethicone crosspolymer. KSG-18 has the INCI name diphenylsiloxy phenyl trimethicone (and) dimethicone/phenyl vinyl dimethicone crossoplymer. Silicone elastomers may also be purchased from Grant Industries under the Gransil trademark. Other suitable silicone elastomers have long chain alkyl substitutions such as lauryl dimethicone/vinyl dimethicone crosspolymers supplied by Shin Etsu under the tradenames KSG-41, KSG-42, KSG-43, and KSG-44, wherein the elastomer is dispersed in solvents including mineral oil, isodocane, triethylhexanoin, or squalene, respectively. Other suitable silicone elastomers may have polyglycerine substitutions such as lauryl dimethicone/polyglycerin-3 crosspolymers supplied by Shin Etsu under the tradenames KSG-810, KSG-820, KSG-830, and KSG-840, wherein the elastomer is dispersed in solvents including mineral oil, isodocane, triethylhexanoin, or squalene, respectively. Other suitable silicone elastomers may have polyglycol substitutions such as PEG-15/lauryl dimethiconecrosspolymers supplied by Shin Etsu under the tradenames KSG-310, KSG-320, KSG-330, and KSG-340, wherein the elastomer is dispersed in solvents including mineral oil, isodocane, triethylhexanoin, or squalene, respectively. Other suitable silicone elastomers having polyglycol substitutions include Shin Etsu's KSG-210, a dimethicone/PEG-10/15 crosspolymer in dimethicone.

Silicone gums are another oil structuring agent. The silicone gum typically has a viscosity ranging from about 500,000 to 100 million cst at 25° C., from about 600,000 to 20 million, from about 600,000 to 12 million cst. Suitable silicone gums include those sold by Wacker-Belsil under the trade names CM3092, Wacker-Belsil 1000, or Wacker-Belsil DM 3096. A particularly suitable silicone gum is dimethiconol, available from Dow Corning Corporation under the trade name 1-1254 Fluid, 2-9023 Fluid, and 2-9026 Fluid. Dimethiconol is often sold as a mixture with a volatile or nonvolatile silicone such as Dow Corning 1401 Fluid, 1403 Fluid, and 1501 Fluid.

Another type of oil structuring agent includes silicone waxes. Silicone waxes may be referred to as alkyl silicone waxes and can be semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from Evonik Goldschmidt GmbH under the tradename Abil Wax 9800 or from Dow Corning under the tradename 2503. Another example is bis-stearyl dimethicone (which may be purchased from Gransil Industries under the tradename Gransil A-18), behenyl dimethicone, or behenoxy dimethicone.

Other suitable viscosity increasing agents include polyamides and polysilicone-polyamide copolymers. Suitable polysilicone-polyamide copolymers are disclosed in U.S. Patent Application Publication No. 2004/0170586. Other oil phase structuring agents may be one or more natural or synthetic waxes such as animal, vegetable, or mineral waxes. Suitable silicone waxes are disclosed in U.S. Pat. Nos. 5,413,781 and 5,725,845, and further include alkylmethyl polysiloxanes, C10-C60alkyl dimethicones, and mixtures thereof. Other structuring agents include natural or synthetic montmorillonite minerals, silicas, silicates, silica silylate, and alkali metal or alkaline earth metal derivatives thereof.

The external phase and internal phases of the micro-scale heterogeneous emulsion may include one or more electrolytes. Non-limiting examples of electrolytes include sodium chloride, potassium chloride, magnesium chloride, and sodium bicarbonate.

Oils may be used to solubilize, disperse, or carry materials that are not suitable for water or water-soluble solvents. Suitable oils include silicones, hydrocarbons, esters, amides, ethers, and mixtures thereof. Oils may be fluid at room temperature. The oils may be volatile or nonvolatile. "Nonvolatile" means a material that exhibits a vapor pressure of no more than about 0.2 mm of mercury at 25° C. at one atmosphere and/or a material that has a boiling point at one atmosphere of at least about 300° C. "Volatile" means that the material exhibits a vapor pressure of at least about 0.2 mm. of mercury at 20° C. Volatile oils may be used to provide a lighter feel when a heavy, greasy film is undesirable. In some examples, oils may be used as carriers associated with the oil phase of a preliminary emulsion.

Suitable oils include volatile oils. In certain embodiments, the volatile oils may have a viscosity ranging from about 0.5 to 5 centistokes at 25° C. Volatile oils may be used to promote more rapid drying after application. Nonvolatile oils are also suitable for use. Nonvolatile oils are often used for their emolliency and protective properties.

Suitable silicone oils include polysiloxanes. Polysiloxanes may have a viscosity of from about 0.5 to about 1,000,000 centistokes at 25° C. Such polysiloxanes can be represented by the general chemical formula:

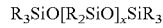

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular weight. In certain embodiments, R is hydrogen, methyl, or ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable dimethicones include those represented by the chemical formula:

wherein R and R are each independently hydrogen or $C_{1-30}$ straight or branched chain, saturated or unsaturated alkyl, aryl, or trialkylsiloxy; and x and y are each integers of 1 to 1,000,000 selected to achieve the desired molecular weight. Suitable silicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone, is available as 2502 Cosmetic Fluid from Dow Corning or as Abil Wax 9801 or 9814 from Evonik Goldschmidt GmbH.

Cyclic silicones are one type of silicone oil that may be used. In certain embodiments, the cyclic silicones may have the general formula:

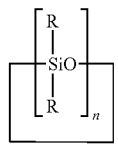

wherein R is independently selected from hydrogen or $C_{1-30}$ straight or branched chain, saturated or unsaturated alkyl, phenyl or aryl, trialkylsiloxy; and where n=3-8 and mixtures thereof. Commonly, a mixture of cyclomethicones is used where n is 4, 5, and/or 6. Commercially available cyclomethicones include Dow Corning UP-1001 Ultra Pure Fluid (i.e. n=4), Dow Corning XIAMETER® PMX-0245 (i.e. n=5), Dow Corning XIAMETER® PMX-0245 (i.e. n=6), Dow Corning 245 fluid (i.e. n=4 and 5), and Dow Corning 345 fluid (i.e. n=4, 5, and 6).

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. The suitable esters typically contain at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters." Other esters suitable for use in the cosmetic composition include those known as polyhydric alcohol esters and glycerides.

Other suitable oils include amides. Amides include compounds having an amide functional group while being liquid at 25° C. and insoluble in water. Suitable amides include N-acetyl-N-butylaminopropionate, isopropyl N-lauroylsarcosinate, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

The micro-scale heterogeneous emulsions may include one or more actives at a safe and effective amount. Preliminary emulsions may be designed to include different actives allowing for flexibility in the design of the micro-scale heterogeneous emulsions. Non-limiting examples of actives include biological, chemical, nutraceutical, and pharmaceutical actives. Non-limiting examples of biological actives include prostaglandins, antimicrobials, antibacterials, biocides, proteins, amino acids, peptides, hormones, growth factors, enzymes (e.g., glutathione sulphydryl oxidase, transglutaminase), therapeutics, oligonucleotides, genetic materials (e.g., DNA, RNA), and combinations thereof. Non-limiting examples of chemical actives include dyes, surfactants, sensates, hair conditioners, hair dyes, hair growth agents, hair removers, hair growth inhibitors, hair styling gels, and combinations thereof. Non-limiting examples of nutraceutical actives may include proteins, vitamins, food-additive materials, and combinations thereof. Non-limiting examples of pharmaceutical actives may include antibiotics, drugs, hair growth agents, hair removers, hair growth inhibitors, small-molecule inhibitors, and combinations thereof. Other useful actives include cationic deposition polymers, deodorizing active ingredients, anti-dandruff agents, film formers, UV actives, antioxidants, insect repellents, antiperspirant actives, occlusive agents, humectants, emollients, skin care actives, tanning actives like dihydroxyacetone, anti-inflammatory actives like hydrocortisone, anti-acne actives like benzoyl peroxide, anti-cellulite agents like xanthine compounds (e.g. caffeine), topical anesthetics like lidocaine, and the like.

Any known natural or synthetic cationic deposition polymer can be used herein. Examples include those polymers disclosed in U.S. Pat. No. 6,649,155; U.S. patent application Ser. No. 12/103,902; U.S. Patent Publication 2008/0206355; and U.S. Patent Publication No. 2006/0099167A1. Non-limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Non-limiting examples of anti-dandruff agents include pyridinethione salts, azoles, selenium sulfide, particulate sulfur, keratolytic acid, salicylic acid, octopirox (piroctone olamine), coal tar, and combinations thereof.

Peptides may contain ten or fewer amino acids where the amino acids includes the derivatives, isomers, and complexes with other species such as metal ions (e.g., copper, zinc, manganese, magnesium, and the like) of the amino acides. Peptide refers to both naturally occurring and synthesized peptides.

Examples of vitamins includes, but are not limited to, water-soluble versions of vitamin B, vitamin B derivatives, vitamin C, vitamin C derivatives, vitamin K, vitamin K derivatives, vitamin D, vitamin D derivatives, vitamin E, vitamin E derivatives, provitamins thereof, such as panthenol and mixtures thereof.

Non-limiting examples of skin care actives include N-undecylenoyl-L-phenylalanine (i.e. undeclenoyl phenylalanine), vitamin B compounds, retinoids, aloe vera, bisabolol, and allantoin. N-undecylenoyl-L-phenylalanine may be commercially available from SEPPIC and sold under the name of Sepiwhite®. N-undecylenoyl-L-phenylalanine is a material that belongs to a broad class of N-acyl phenylalanine derivatives and is known as a topical skin tone evening agent. As used herein, vitamin B compounds include B1 compounds, B2 compounds, B3 compounds such as niacinamide, B5 compounds, such as panthenol or "pro-B5", pantothenic acid, pantothenyl, B6 compounds, such as pyroxidine, pyridoxal, pyridoxamine, carnitine, thiamine, and riboflavin. In some embodiments, the vitamin B compound is a B3 compound having the formula:

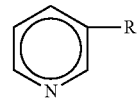

wherein R is $-CONH_2$ (i.e., niacinamide), $-COOH$ (i.e., nicotinic acid) or $-CH2OH$ (i.e., nicotinyl alcohol); derivatives thereof; and salts of any of the foregoing. "Retinoid" as used herein means natural and synthetic analogs of Vitamin A, or retinol-like compounds which possess the biological activity of Vitamin A in the skin, as well as the geometric isomers and stereoisomers of these compounds. The retinoid may be selected from retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), or mixtures thereof.

As used herein, "UV active" includes both sunscreen agents and physical sunblocks. Suitable UV actives may be organic or inorganic. Suitable UV actives are listed in the functional category of "Sunscreen Agents" in the Personal Care Product Council's *International Cosmetic Ingredient Dictionary and Handbook*, Thirteenth Edition, 2010. Suitable UV actives include those defined or proposed by regulatory agencies in the US (e.g., 21 CFR part 352, 68 Federal Register 41386, 70 Federal Register 72449, or 71 Federal Register 42405), Europe (Regulation No 1223/2009 of the EU Parliament; Annex VI), Japan, China, Australia, New Zealand, or Canada. For example, the micro-scale heterogeneous emulsion may comprise from about 0.01% to about 20%, by weight of the cosmetic composition, of a UV active. The micro-scale heterogeneous emulsion may also comprise a sufficient amount of UV active to yield a Sun Protection Factor of at least about 15, 30 45, or 50. SPF testing is conventional and well understood in the art. A suitable SPF test is prescribed in 21 C.F.R. 352, Subpart D.

Suitable UV actives include dibenzoylmethane derivatives including 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxy dibenzoylmethane, 4-tert-butyl-4'-methoxy dibenzoylmethane (i.e., butyl methoxydibenzoylmethane or avobenzone) (commercially available as PARSOL® 1789 from DSM), 2-methyl-5-isopropyl-4'-methoxy dibenzoylmethane, 2-methyl-5-tert-butyl-4'-methoxydibenzoylmethane, 2,4-dimethyl-4'-methoxy dibenzoylmethane, and 2,6-dimethyl-4-tert-butyl-4'-methoxy dibenzoylmethane. Other suitable UV actives include 2-ethylhexyl-p-methoxycinnamate (commercially available as PARSOL® MCX from DSM), 2-hydroxy-4-methoxybenzophenone, benzonphenone-3 (i.e. oxybeznone), octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, titanium dioxide, and mixtures thereof.

Particularly suitable UV actives are 2-ethylhexyl-p-methoxycinnamate, 4-tert-butyl-4'-methoxy dibenzoylmethane, 2-hydroxy-4-methoxybenzo-phenone, 2-phenylbenzimidazole-5-sulfonic acid, octocrylene, zinc oxide, titanium dioxide, and mixtures thereof.

Other suitable UV actives include 4-methylbenzylidene camphor (commercially available as PARSOL® 5000 from DSM or Eusolex 6300 from Merck), methylene bis-benzotriazolyl tetramethylbutylphenol (i.e., bisoctrizole, commercially available as Tinosorb® M from BASF), bis-ethylhexyloxyphenol methoxyphenol triazine (i.e., bemotrizinol, commercially available as Tinosorb® S from BASF), disodium phenyl dibenzimidazole tetrasulfonate (i.e., Bisdisulizole disodium, commercially available as Neo Heliopan® AP from Symrise), Ethylhexyl triazone (commercially available as Uvinul® T 150 from BASF), Drometrizole trisiloxane (marketed as Mexoryl XL by L'Oreal), Sodium Dihydroxy Dimethoxy Disulfobenzophenone (i.e., benzophenone-9, commercially available as Uvinul® DS 49 from BASF), Diethylamino Hydroxybenzoyl Hexyl Benzoate (commercially available as Uvinul® A Plus from BASF), diethylhexyl butamido triazone (i.e., Iscotrizinol, commercially available as Uvasorb® HEB by 3V Sigma), Polysilicone-15 (i.e., commercially available as PARSOL® SLX from DSM), and Isoamyl p-Methoxycinnamate (i.e., amiloxate, commercially available as Neo Heliopan® E 1000 from Symrise).

Non-limiting examples of antiperspirant actives include aluminum/zirconium astringent complexes including aluminum halides, aluminum hydroxy-halides, zirconyl oxyhalides, zirconyl hydroxy-halides; and ZAG complexes such as aluminium zirconium trichlorohydrex gly.

Non-limiting examples of occlusive agents include petrolatum, mineral oil, lanolin, paraffin, beeswax, and cocoa butter. Non-limiting examples of humectants include urea, glycerin, sorbitol, honey, and hyaluronic acid. Non-limiting examples of emollients include octyl dodecanol, oleyl alcohol, and myristyl myristate. Other examples of actives include guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fucose); hyaluronic acid; lactamide monoethanolamine; acetamide monoethanolamine; panthenol; allantoin; and mixtures thereof. Also useful herein are the propoxylated glycerols described in U.S. Pat. No. 4,976,953. Also useful are various $C_1$-$C_{30}$ monoesters and polyesters of sugars and related materials. These esters are derived from a sugar or polyol moiety and one or more carboxylic acid moieties.

Other non-limiting examples of actives also include extracts such as *Laminaria Saccharina* extract and *Ficus Bengalensis* extract, sugar amines, phytosterols, salicylic acid compounds, hexamidines, dialkanoyl hydroxyproline compounds, botanicals, N-acyl amino acid compounds, their derivatives, and combinations thereof. Exemplary sugar amines suitable for use herein are described in PCT Publication No. WO 02/076423 and U.S. Pat. No. 6,159,485. Sugar amines can be synthetic or natural in origin and can be used as pure compounds or mixtures of compounds (e.g., extracts from natural sources or mixtures of synthetic materials). A particularly suitable example of a sugar amine is glucosamine and its salts, which may be found in certain shellfish or derived from fungal sources. Other examples of sugar amines include N-acetyl glucosamine, mannosamine, N-acetyl mannosamine, galactosamine, N-acetyl galactosamine, their isomers (e.g., stereoisomers), and their salts (e.g., HCl salt). Flavonoids are broadly disclosed in U.S. Pat. Nos. 5,686,082 and 5,686,367. Examples of some flavonoids are one or more flavones, one or more isoflavones, one or more coumarins, one or more chromones, one or more dicoumarols, one or more chromanones, one or more chromanols, isomers (e.g., cis/trans isomers) thereof, and mixtures thereof. Some examples include flavones and isoflavones, such as daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof. Flavonoid compounds useful herein are commercially available from a number of sources, e.g., Indofine Chemical Company, Inc., Steraloids, Inc., and Aldrich Chemical Company, Inc.

The micro-scale heterogeneous emulsions may also include a chelating agent such as furildioxime and its derivatives. In addition to the previously described ingredients, the micro-scale heterogeneous emulsions described herein may also comprise one or more other ingredients as described in U.S. Publications Nos. US2002/0022040; US2003/0049212; US2007/0196344; US2008/0181956; US2010/00092408; US2008/0206373; US 2010/0239510; US2010/0189669; US2011/0262025; US2011/0097286; US2012/0197016; US2012/0128683; US2012/0148515; US2012/0156146; and US2013/0022557 and U.S. Pat. Nos. 5,939,082; 5,872,112; 6,492,326; 6,696,049; 6,524,598; 5,972,359; and 6,174,533.

The micro-scale heterogeneous emulsion may also include one or more fragrances. As used herein, "fragrance" is used to indicate any odoriferous material. In some examples, fragrances that are cosmetically acceptable may be used. A wide variety of chemicals are known as fragrances, including aldehydes, ketones, and esters. More commonly, naturally occurring plant and animal oils and exudates comprising complex mixtures of various chemical components are known for use as fragrances. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of ways. For example, the fragrance may be released as a result of simple hydrolysis, or by a shift in an equilibrium reaction, or by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor.

The fragrances may have a boiling point (BP) of about 500° C. or lower, about 400° C. or lower, or about 350° C. or lower. The BP of many fragrances are disclosed in *Perfume and Flavor Chemicals* (Aroma Chemicals), Steffen Arctander (1969). The ClogP value of the fragrances may be about 0.1 or greater, about 0.5 or greater, about 1.0 or greater, and about 1.2 or greater. As used herein, "ClogP" means the logarithm to the base 10 of the octanol/water partition coefficient. The ClogP can be readily calculated from a program called "CLOGP" which is available from Daylight Chemical Information Systems Inc., Irvine Calif., USA. Octanol/water partition coefficients are described in more detail in U.S. Pat. No. 5,578,563.

Suitable fragrances are also disclosed in U.S. Pat. No. 4,145,184, 4,209,417, 4,515,705, and 4,152,272. Non-limiting examples of fragrances include animal fragrances such as musk oil, civet, castoreum, ambergris, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, *eucalyptus* oil, *verbena* oil, *mimosa* extract, *narcissus* extract, carrot seed extract, jasmine extract, olibanum extract, rose extract, and mixtures thereof.

Other examples of suitable fragrances include, but are not limited to, chemical substances such as acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, cis-3-hexenyl methyl carbonate, citral, citronnellol and ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltolide, fenchone, fruity esters such as ethyl 2-methyl butyrate, galaxolide, geraniol and ester derivatives, helional, 2-heptonone, hexenol, α-hexylcinnamic aldehyde, hydroxycitrolnellal, indole, isoamyl acetate, isoeugenol acetate, ionones, isoeugenol, isoamyl iso-valerate, iso E super, limonene, linalool, lilial, linalyl acetate, lyral, majantol, mayol, melonal, menthol, p-methylacetophenone, methyl anthranilate, methyl cedrylone, methyl dihydrojasmonate, methyl eugenol, methyl ionone, methyl-α-naphthyl ketone, methylphenylcarbinyl acetate, mugetanol, γ-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohexanol, γ-undecalactone, undecenal, vanillin, veloutone, verdox, and mixtures thereof.

Methods of Use

The micro-scale heterogeneous emulsions may be used, for example, in consumer products. For example, the micro-scale heterogeneous emulsion may be a consumer product provided in a package sized to store a sufficient amount of the micro-scale heterogeneous emulsion. The size, shape, and design of the package may vary widely. Certain package examples are described in U.S. Pat. Nos. D570,707; D391,162; D516,436; D535,191; D542,660; D547,193; D547,661; D558,591; D563,221; 2009/0017080; 2007/0205226; and 2007/0040306.

In some examples, the micro-scale heterogeneous emulsion may be provided as a consumer product intended to be used or consumed in the form in which it is sold, and not intended for subsequent commercial manufacture or modification.

In some examples, the micro-scale heterogeneous emulsion may be used in a method for providing a stable, custom cosmetic composition. By "custom" it is meant that the consumer product is made-to-order. In some examples, a consumer may be provided a list of active options, a list of fragrance options, a list of color options, and combinations thereof. In some examples, the consumer may also be provided options of packages for packaging the micro-scale heterogeneous emulsion. In some examples, a consumer may receive an instruction that may encompass more than one option that may be included in a micro-scale heterogeneous emulsion. In some examples, the consumer may be instructed by any known method of instructing. Non-limiting examples of the potential ways for instructing include involving a salesperson or other individual, involving a sign, involving the internet, involving an advertisement, word of mouth, involving a catalog, involving printed material, involving non-verbal communication, etc. In some examples, the consumer may be instructed to select at least one active, a fragrance, a color, a package, and combinations thereof. In some examples, the micro-scale heterogeneous emulsion is prepared based on the consumer's selections. In some examples, the different emulsions used to make the micro-scale heterogeneous emulsion are combined in the consumer's vicinity. In some examples, only the dispersions used in making the micro-scale heterogeneous emulsion are combined in the consumer's vicinity. In some examples, the combining occurs within the consumer's vicinity when the combining occurs within the store or location where the consumer is located. In some examples, the different emulsions used to make the micro-scale heterogeneous emulsion are combined remotely (i.e. not within the consumer's vicinity). In some examples, the consumer combines the emulsions and optionally the dispersions to form the final micro-scale heterogeneous emulsion. In some examples, the consumer combines the dispersion(s) with a micro-scale heterogeneous emulsion. In some examples, the consumer performs the step of combining to form the micro-scale heterogeneous emulsion.

EXAMPLES

The following examples are given solely for the purpose of illustration and are not to be construed as limiting the invention, as many variations thereof are possible.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

Example 1

Micro-Scale Heterogeneous Emulsion

TABLE 1

Preliminary Emulsion 1

| Component | Amount |
|---|---|
| Water | QS |
| Cyclopentasiloxane | 18.234% |
| PEG/PPG 18/18 Dimethicone and Cyclopentasiloxane | 4% |
| Sodium Chloride | 3.766% |
| Hexanediol and Caprylyl Glycol | 0.5% |
| Phenoxyethanol | 0.250% |
| Benzyl Alcohol | 0.250% |
| Total | 100% |

TABLE 2

Preliminary Emulsion 2

| Component | Amount |
| --- | --- |
| Cyclopentasiloxane and Dimethicone Crosspoylmer | QS |
| Glycerin | 18.568% |
| Niacinamide | 5.305% |
| Diethylhexyl Carbonate | 5.305% |
| Panthenol | 1.326% |
| Tocopheryl Acetate | 1.326% |
| Dimethicone and PEG 10 Dimethicone Crosspolymer | 1.326% |
| Allantoin | 0.531% |
| Total | 100% |

TABLE 3

Preliminary Emulsion 3

| Component | Amount |
| --- | --- |
| Cyclopentasiloxane | QS |
| PEG/PPG 18/18 Dimethicone and Cyclopentasiloxane | 5.436% |
| DIMETHICONE 350CS | 7.373% |
| DIMETHICONE 50CS | 11.060% |
| Arachidyl Behenate | 1.106% |
| Synthetic Wax | 0.369% |
| Trihydroxystearin | 1.106% |
| Silica | 0.369% |
| Talc, Ethylene/Methacrylate Copolymer and Isopropyl Titanium Triisostearate | 1.843% |
| Aluminum Starch Octenylsuccinate | 9.217% |
| Ethylene Brassylate | 0.184% |
| Polyglyceryl-4 isostearate and Cetyl dimethicone | 0.737% |
| Propylene Glycol | 29.494% |
| PVP-K-17 | 3.687% |
| Total | 100% |

To make Preliminary Emulsion I, begin by preparing a water-premix by propeller mixing the water, sodium chloride, phenoxyethanol, benzyl alcohol, hexanediol, and caprylyl glycol in a pre-mix tank until all the solids are fully dissolved and liquids fully blended. Next, add the cyclopentasiloxane and the PEG/PPG-18/18 dimethicone and cyclopentasiloxane directly to a Giusti main-mix tank. Begin scrapewall mixing at 49 RPMs and inner agitator mixing at 69 RPM the contents in the Giusti main-mix tank. Turn on the homogenizer and set to 1500 RPM. Transfer the water-premix using a Waukesha positive displacement transfer pump such that the transfer time takes greater than 10 minutes. During water transfer, slowly increase the homogenizer speed 250 RPMs every 2 minutes until the homogenizer speed is 3000 RPM. After the transfer is complete, turn the recirculation on at 62 RPM. Continue mixing at 3000 RPM with the scrapewall mixing at 49 RPM and the inner agitator mixing at 69 RPM for an additional 15 minutes. After about 15 minutes, turn off all mixing. Pump out the material at 62 RPM into an approved fiber drum and store in an appropriate fiber drum.

To make Preliminary Emulsion 2, first mix the glycerin, niacinamide, panthenol, and allantoin in a tank with a lightnin' mixer until the solids are dispersed and homogeneous. Heat the mixture as necessary to dissolve the solid ingredients. Next in a plastic 5 gallon bucket, mix the diethylhexyl carbonate, totpheryl acetate, and dimethicone and dimethicone copolyol crosspolymer with a spatula until the liquids are well blended and homogeneous. This step should last about 1-2 minutes. Next, mix the mixture of diethylhexyl carbonate, tocopheryl acetate, and dimethicone and dimethicone copolyol crosspolymer with the cyclopentasiloxe and dimethicone cros spolymer-DC9040 in the Giusti vessel and turn on the inner and outer agitators to 49 RPM and 39 RPM, respectively. After 5 minutes, turn on the homogenizer at 3000 RPM and turn on the cooling water to maintain temperature at less than 35° C. Adjust the mix speeds and times as necessary. Transfer the mixture of glycerin, niacinamide, panthenol, and allantoin into the Giusti vessel while continuing to mix. Continue mixing for 10-15 minutes until the product is homogeneous then store the product in an appropriate container.

To make Preliminary Emulsion 3, first combine trihydroxystearin and approximately 2% of the cyclopentasiloxane in a small container. Mix with a propeller mixer or by hand with a spatula to fully disperse the trihydroxystearin and create a thixcin pre-mix. Next, combine the remaining cyclopentasiloxane, PEG/PPG 18/18 Dimethicone and Cyclopentasiloxane, Dimethicone 350CS, and Dimethicone 50CS ingredients in a main mix tank (Giusti). Begin mixing with the inner and outer agitators at 49 and 69 RPM. Add ingredients Arachidyl Behenate and Synthetic Wax to the main mix tank and begin heating to 90 C+/−5 C. While heating, mix the batch with the inner and outer agitators at 49 and 69 RPM and homogenizer at 3000 RPM. Once the target temperature range is reached, continue mixing for 5 minutes. After 5 minutes, discontinue the high shear mixing and start cooling to 55 C+/−5 C. With the main mix tank at 55 C+/−5 C, add the Thixcin pre-mix and begin high shear mixing with the homogenizer overnight at 3000 RPM. Cool the silicone phase down to 25 C+/−5 C while continuing to high shear mix with the homogenizer overnight. Add the final silicone phase ingredients Silica, Talc, Ethylene/Methacrylate Copolymer and Isopropyl Titanium Triisostearate, Aluminum Starch Octenylsuccinate, and Ethylene brassylate. Continue mixing for 5 minutes with the homogenizer ON at 3000 RPM, agitator and scrapewall overnight at 69 and 49 RPM respectively.

In a separate pre-mix vessel, add ingredients Polyglyceryl-4 isostearate and Cetyl dimethicone copolyol and hexyl laurate, and Propylene glycol and begin agitation with a propeller mixer. Slowly add PVP-K-17 to the water pre-mix tank. Continue mixing until the PVP-K-17 is fully dispersed. Heat may be used to facilitate the process if needed. Record the maximum temperature. Once the polymer solution is homogeneous, begin cooling to 25 C+/−5 C. Transfer the propylene glycol phase using a waukesha positive displacement transfer pump such that the transfer time takes greater than 5 minutes. During transfer, mix with the homogenizer ON at 3000 RPM, the outer agitator overnight at 49 RPM and the inner agitator overnight (ON) at 69 RPM. After transfer is complete, continue mixing with the homogenizer ON at 3000 RPM, the outer agitator ON at 49 RPM and the inner agitator ON at 69 RPM for an additional 15 minutes. After 15 minutes, turn off all mixing. Pump out the material at 62 RPM into an approved fiber drum.

To prepare the micro-heterogeneous emulsion, combine an amount of Preliminary Emulsion 1, Preliminary Emulsion 2, and Preliminary Emulsion 3 by low shear mixing. The amount of premix will depend on the desired amount of the ingredients to be included in the final micro-scale heterogeneous emulsion. The low shear mixing may be performed by using a lightnin' mixer with a pitched blade turbine mixer geometry.

Example 2

Niacinamide Measurements

The emulsions set forth in FIG. 8 were prepared from the ingredients described in TABLES 4, 6, and 7 below. A batch process emulsion (denoted as Batch Emulsion in FIG. 8) was prepared from the ingredients listed in TABLE 4. Briefly, in a 1000 ml stainless steel beaker, combine Part A ingredients and mix with a Lightnin' mixer until the solids are dispersed and homogeneous. In a 1000 ml jacketed vessel, mix the Part B ingredients with a lightnin' mixer until the liquids are well blended and homogeneous. Next, in a 1000 ml jacketed vessel, mix the Part B ingredients with the Part C ingredient with a large circle Silverson attachment at 2500 RPM for 5 minutes until homogeneous. Transfer the two separate phases into individual containers. Aliquots of Table 4 part A were then spiked with $^{14}$C-niacinamide with approximately 3 µCi per 300 mg product aliquot and mixed with a spatula to disperse the active in the polar phase. Part A with the radiotagged niacinamide and B/C were then emulsified together utilizing a micro-mixer from Sigma Aldrich (Wig-L-Bug mixer) at the specified ratios shown in TABLE 5.

TABLE 4

| | Ingredient | Wt % |
|---|---|---|
| Part A | Water | 30.234 |
| | Sodium Chloride | 1.399 |
| | Phenoxyethanol | 0.373 |
| | Benzyl Alcohol | 0.373 |
| | Sodium Benzoate | 0.047 |
| | Glycerin | 9.929 |
| | Niacinamide | 2.837 |
| | Dexpanthenol | 0.709 |
| | Allantoin | 0.284 |
| Part B | Cyclopentasiloxane | 11.774 |
| | PEG/PPG 18/18 Dimethicone and Cyclopentasiloxane | 2.326 |
| | Dimethicone and PEG 10 Dimethicone Crosspolymer | 0.709 |
| | Diethyl Hexyl Carbonate | 2.837 |
| | Tocopherol Acetate | 0.709 |
| Part C | Cyclopentasiloxane and Dimethicone Crosspoylmer | 35.460 |
| | Total | 100% |

TABLE 5

| Batch | Wt % | Parts |
|---|---|---|
| Table 4 Part A | 46.18% | 32.56 |
| Table 6 | 53.82% | 37.94 |
| Part B/C | | |
| | 100.00% | 70.5 |

Micro-Scale Heterogeneous Emulsion I was prepared from the ingredients listed in TABLES 6 and 7 at the ratios specified in Table 8. To prepare Micro-Scale Heterogeneous Emulsion I, prepare a mix of the Part A ingredients from TABLE 6 by mixing the ingredients with a lightnin' mixer in a 1000 ml stainless steel beaker until the solids are dispersed and homogeneous. Next, mix the Part B ingredients from TABLE 6 with a lightnin' mixer in a 1000 ml jacketed vessel until the liquids are well blended and homogeneous. Next, combine the mixture of the Part B ingredients with the Part C ingredients from TABLE 6 using a large circle silverson attachment at 2500 RPM for 5 minutes in the 1000 ml jacketed vessel. Transfer the two separate phases into individual containers. Aliquots of the Part A from Table 6 were then spiked with $^{14}$C-niacinamide with approximately 3 µCi per 300 mg product aliquot and mixed with a spatula to disperse the active in the polar phase. Part A with the radiotagged niacinamide and Part B/C were then emulsified together utilizing a micro-mixer from Sigma Aldrich (Wig-L-Bug mixer).

TABLE 6

| | Ingredient | % Weight |
|---|---|---|
| Part A | Glycerin | 18.568 |
| | Niacinamide | 5.305 |
| | Dexpanthenol | 1.326 |
| | Allantoin | 0.531 |
| Part B | Dimethicone and PEG 10 Dimethicone Crosspolymer | 1.326 |
| | Diethyl Hexyl Carbonate | 5.305 |
| | Tocopherol Acetate | 1.326 |
| Part C | Cyclopentasiloxane and Dimethicone Crosspoylmer | 66.313 |
| | Total | 100 |

Next make a water-premix from the ingredients listed in TABLE 7. Begin by preparing a water-premix by propeller mixing Parts 1-5 in a pre-mix tank until all the solids are fully dissolved and liquids fully blended. Next, add the cyclopentasiloxane and the PEG/PPG-18/18 dimethicone and cyclopentasiloxane directly to a Giusti main-mix tank. Begin scrapewall mixing at 49 RPMs and inner agitator mixing at 69 RPM the contents in the Giusti main-mix tank. Turn on the homogenizer and set to 1500 RPM. Transfer the water-premix using a Waukesha positive displacement transfer pump such that the transfer time takes greater than 10 minutes. During water transfer, slowly increase the homogenizer speed 250 RPMs every 2 minutes until the homogenizer speed is 3000 RPM. After the transfer is complete, turn the recirculation on at 62 RPM. Continue mixing at 3000 RPM with the scrapewall mixing at 49 RPM and the inner agitator mixing at 69 RPM for an additional 15 minutes. After about 15 minutes, turn off all mixing. Pump out the material at 62 RPM into a storage container.

TABLE 7

| Part | Ingredient | % Weight |
|---|---|---|
| 1 | Deionized Water | 65 |
| 2 | Sodium Chloride | 3 |
| 3 | Phenoxyethanol | 0.8 |
| 4 | Sodium Benzoate | 0.8 |
| 5 | Benzyl Alcohol | 0.1 |
| 6 | Cyclopentasiloxane | 25.30 |
| 7 | PEG/PPG 18/18 Dimethicone and Cyclopentasiloxane | 5 |
| | Total | 100 |

The active and radio tagged containing preliminary emulsion was then combined with the non-active containing preliminary emulsion shown in TABLE 7 to form micro-heterogeneous emulsion at the specified ratios in TABLE 8. The mixing was completed by using a spatula.

TABLE 8

| Micro-Scale Heterogeneous Emulsion I | Wt % | Parts |
|---|---|---|
| Table 6 - Part A | 13.76% | 9.7 |
| Table 6 - Part B/C | 39.72% | 28 |
| Table 7 | 46.52% | 32.8 |
| | 100.00% | 70.5 |

Micro-Scale Heterogeneous Emulsion II was prepared from the ingredients listed in TABLES 6 and 7. To prepare Micro-Scale Heterogeneous Emulsion II, prepare a mix of the Part A ingredients from TABLE 6 by mixing the ingredients with a lightnin' mixer in a 1000 ml stainless steel beaker until the solids are dispersed and homogeneous. Next, mix the Part B ingredients from TABLE 6 with a lightnin' mixer in a 1000 ml jacketed vessel until the liquids are well blended and homogeneous. Next, in a 3000 ml jacketed vessel, mix the Part B premix of ingredients from TABLE 6 with Part C of TABLE 6 and mix with the large circle silverson attachment at 2500 RPM for 5 minutes. Next, emulsify Table 6 part A into Table 6 part B/C utilizing a silverson mixer at 6000 RPM in the 3000 mL jacketed vessel until the sample is fully homogenous. Store Table 6 combined product in a container. Aliquots of product from Table 6 were then spiked with $^{14}$C-niacinamide with approximately 3 μCi per 300 mg product aliquot and mixed with a spatula to disperse the active in the product. The resultant radiotagged niacinamide formulation was then combined with product from Table 7 at the ratios specified in Table 9. The mixing was completed using a spatula.

TABLE 9

| Micro-Scale Heterogeneous Emulsion II | Wt % | Parts |
|---|---|---|
| Table 6 - Combined | 53.48% | 37.7 |
| Table 7 | 46.52% | 32.8 |
| | 100.00% | 70.5 |

Split thickness cadaver skin was obtained from AlloSource (Englewood, Colo.). Tritiated water was from PerkinElmer (Boston, Mass.) while $^{14}$C niacinamide was obtained from American Radiochemicals (St. Louis, Mo.). For all studies, split-thickness human cadaver skin was maintained at −70° C. until thawed at ambient conditions, rinsed with distilled water, cut into appropriately sized sections, and mounted in standard Franz-type diffusion cells (0.79 cm$^2$) which were placed in heating/stirring blocks thermostatted to maintain a skin surface temperature of about 34° C. The receptors [~5 mL] were filled with a solution of 1% polysorbate 20 (VWR International, West Chester, Pa.) in Dulbecco's Phosphate Buffered Saline [PBS] (Sigma-Aldrich, Inc., St. Louis, Mo.) with agitation provided by magnetic stir bars, and the skin allowed to equilibrate for at least two hours.

Next, human cadaver skin samples were mounted in standard Franz-type diffusion cells (0.79 cm$^2$ surface area) maintained at about 37° C. Six replicates for each compositional leg were prepared. The receptor compartments were filled with 5 mL phosphate buffered saline (PBS—pH 7.4) that included 1% polysorbate-20 and 0.02% sodium azide, and the skin allowed to equilibrate for two hours. The cells were randomized to treatment group based upon $^3$H$_2$O flux through the mounted skin (150 μL of $^3$H2O applied for five minutes, removed and followed by collection of receptor fluid after 60 minutes). Diffusion cells were randomized by ranking each cell according to water flux and distributing cells across treatment legs such that each group included cells across the range of observed water flux. Each treatment group typically had 6 replicates.

Aliquots of the batch emulsion and micro-scale heterogeneous emulsions I & II which were previously spiked with $^{14}$C-niacinamide, approximately 3 μCi per 300 mg product aliquot, were mixed and assayed for total radioactivity in triplicate using Ultima Gold (available from Perkin-Elmer) liquid scintillation cocktail (LSC) and liquid scintillation counting (Tri-Carb 2500 TR Liquid Scintillation Analyzer, PerkinElmer, Boston, Mass.). The skin samples were topically dosed with 5 μL of the radiolabeled niacinamide emulsion using a positive displacement pipette. The emulsions was gently spread over the surface of the skin samples (0.79 cm$^2$) using the pipet tip. The receptor solution was collected and replaced at 6 hours following application with a final collection at 24 hrs. After the final receptor collection, each skin sample was wiped two times with Whatman filter paper soaked with PBS/Tween 20 and once with 70%/30% ethanol/water to remove unabsorbed (residual) product. The epidermis was separated from the residual dermis by dissection. The skin sections were dissolved in 0.50-1.25 mL Soluene-350 (Perkin Elmer, Boston, Mass.) at 60° C. overnight, and all receptor collections, filter paper wipes, and solubilized tissue sections were counted using liquid scintillation counting. Disintegrations-per-minute (DPM) for each compartment of each cell were blank corrected and summed to obtain a total recovered radiolabel value for a given cell. The DPM of each compartment were then normalized to the total recovered radiolabel value to obtain a "percent recovered radiolabel" parameter for each compartment (individual receptor collections, epidermis, dermis, and wipes for mass balance). Cumulative receptor values to each collection time point were calculated as the sum of the individual collections to that time point, with the total receptor value as the sum of all individual collections. The total recovered percentage value was the sum of the epidermis (including stratum corneum) and dermis values, and the total permeated value the sum of total skin and cumulative receptor values. FIG. 8 summarizes the total percentage values of radiolabeled niacinamide recovered.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product which is a cosmetic composition for treating keratinous tissue, comprising a micro-scale heterogeneous emulsion, the micro-scale heterogeneous emulsion comprising: at least a first internal phase and a second internal phase each dispersed as droplets in an aqueous external phase, wherein
the droplets of the first internal phase comprise at least one of silicone oils, hydrocarbon oils, ester oils, amide oils, ether oils, or combinations thereof;
the droplets of the second internal phase comprise a core at least of a non-aqueous polar solvent and a membrane at least of a silicone oil;
the droplets of the first internal phase and the droplets of the second internal phase are each stabilized within the external phase, are separate from each other, and the droplets do not substantially exhibit droplet coalescence;
the second internal phase differs at least in part from the first internal phase in chemical makeup; and
the droplets of the first internal phase have an overall size of 0.5 microns to 100 microns.

2. A product according to claim 1 wherein the internal phases are substantially free of destabilizing constituents.

3. A product according to claim 2 wherein the destabilizing constituents include at least benzyl alcohol, ethyl alcohol, phenoxyalcohol or combinations thereof.

4. A product according to claim 1 wherein the internal phases further comprise stabilizers.

5. A product according to claim 4 wherein the stabilizers include surfactants, functionally modified polymers or combinations thereof.

6. A product according to claim 5 wherein the stabilizers include silicone surfactants, non-ionic surfactants, ionic surfactants, cationic surfactants, anionic surfactants, ethers and esters of polyglycols and fatty acids, linear or branched silicone emulsifiers, silicone elastomers or combinations thereof.

7. A product according to claim 1 wherein the internal phases include one or more structuring agents.

8. A product according to claim 7 wherein the structuring agents include silicone elastomers, silicone gums, silicone waxes, linear silicones, natural waxes, synthetic waxes, natural or synthetic monmorillonite minerals, silicas, silicates, silica silylate, alkali metal or alkaline earth metal derivatives of any of the silicone gums, waxes, natural or synthetic waxes, minerals, silicas, silicates, silica silyate, polyamides, polysilicone-polyamide copolymers or any combination thereof.

9. A product according to claim 1 wherein the droplets of one of the first and second internal phases contain an active selected from the group consisting of a biologically active, a cosmetic ingredient, a fragrance, a color and a combination thereof.

10. A product according to claim 9 wherein the droplets of both of the first and second internal phases contain an active.

11. A product according to claim 10 wherein the active of the droplets of the first internal phase differ from the active of the droplets of the second internal phase.

12. A product according to claim 1 further comprising multiple internal phases dispersed as droplets in the aqueous external phase and the droplets of the internal phases except the first phase comprise cores and membranes of immiscible non-aqueous components.

13. A product according to claim 12 wherein the first internal phase comprises substantially homogeneous droplets of non-aqueous components.

* * * * *